US005676950A

United States Patent [19]

Small, Jr. et al.

[11] Patent Number: 5,676,950
[45] Date of Patent: Oct. 14, 1997

[54] ENTERICALLY ADMINISTERED RECOMBINANT POXVIRUS VACCINES

[75] Inventors: Parker A. Small, Jr.; Bradley Stephen Bender, both of Gainesville, Fla.; Catherine Ann Meitin, Lake Oswego, Oreg.; Bernard Moss, Bethesda, Md.

[73] Assignee: University of Florida, Gainesville, Fla.

[21] Appl. No.: 485,229

[22] Filed: Jun. 7, 1995

Related U.S. Application Data

[63] Continuation-in-part of Ser. No. 330,641, Oct. 28, 1994, abandoned.
[51] Int. Cl.$^6$ .......................... A61K 39/12; A61K 39/245; A61K 9/48; A61K 9/00
[52] U.S. Cl. ............................ 424/199.1; 424/232.1; 424/463; 424/474; 424/490; 424/400; 435/235.1
[58] Field of Search ................................ 424/199.1, 232.1, 424/463, 474, 490, 400; 435/235.1

[56] References Cited

U.S. PATENT DOCUMENTS

| | | | |
|---|---|---|---|
| 4,920,209 | 4/1990 | Davis et al. | 435/235.1 |
| 5,174,993 | 12/1992 | Paoletti | 424/199.1 |

FOREIGN PATENT DOCUMENTS 1333512  10/1973  United Kingdom.

OTHER PUBLICATIONS

Kanesaki, T. et al. (1991) "Effectiveness of Enteric Immunization in the Development of Secretory Immunoglobulin A Response and the Outcome of Infection with Respiratory Syncytial Virus" Journal of Virology 65(2)657–663.

Hochstein–Mintzel, V. et al. (1972) "Oral and Nasal Immunization with Poxvirus Vaccinaiae 3rd Communication: Animal Experiments" Zentralb. Bacteriol. (orig B) 156:30–96.

Andrew, M.E. et al. (1987) "The Roles of Influenza Virus Haemagglutinin and Nucleoprotein Protection: Analysis Using Vaccinia Virus Recombinants" Scand. J. Immunol. 25:21–28.

Bender, B.S. et al. (1990) "Cytotoxic–T–lymphocyte Activity Induced by Influenza Vaccination in Young and Aged Mice" Vaccines 90:69–73.

Bennink, J.R. et al. (1984) "Recombinant vaccinia virus primes and stimulates influenza haemagglutinin–specific cytotoxic T cells" Nature 311:578–579.

Blancou, J. et al. (1986) "Oral Vaccination of the fox against rabies using a live recombinant vaccinia virus" Nature 322:373–375.

Fenner, F. et al. (1988) "Smallpox and its Eradication" World Health Organization–Geneva, p. 465.

Gibbons, A. (1994) "Children Vaccine Initiative Stumbles" Science 265:1376–1377.

Greer, K.E., C.N. Sheap (1974) "A Family Outbreak of Oral Accidential Vaccinia" Arch. Dermatol. 110:107–108.

Lin, Y.–L., B.A. Askonas (1981) "Biological Properties of an Influenza A Virus–Specific Killer T Cell Clone" J. Exp. Med. 154:225–234.

Loosli, C.G., D. Hamre, B.S. Berlin (1953) "Air–Borne Influenza Virus A Infections in Immnized Animals" Trans. Assoc. Am. Phys. 66:222–230.

Meitin, C.A., B.S. Bender, P.A. Small Jr. (1991) "Influenza immunization: intranasal live vaccinia recombinant contrasted with parental inactivated vaccine" Vaccine 9:751–755.

Meitin, C.A., P.A. Small, Jr. (1993) "Scarification with a vaccinia–influenza recombinant does not stimulate IgA unless the animals auto–or cross–inoculate their nasopharynxes" Vaccine 11(13):1360–1362.

Perkus, M.E. et al. (1985) "Recombinant Vaccinia Virus: Immunizatin AGainst Multiple Pathogens" Science 229:981–984.

Renegar, K.B., P.A. Small, Jr. (1991) "Immunoglobulin A Mediation of Murine Nasal Anti–Influenza Virus Immunity" Journal of Virology 65(4):2146–2148.

Renegar, K.B., P.A. Small, Jr. (1991) "Passive Transfer of Local Immunity to Influenza Virus Infection by IgA Antibody" The Journal of Immunology 146(6):1972–1978.

Rupprecht, C.E., M.–P., Kieny (1988) "Development of Vaccinia–Rabies Glycoprotein Recombinant Virus Vaccine" Rabies: Developments in Veterinary Virology 335–364.

Rupprecht, C.E. et al. (1986) "Oral immunization and protection of raccoons (*Procyon lotor*) with a vaccinia–rabies glycoprotein recombinant virus vaccine" Proc. Natl. Acad. Sci. USA 83:7947–7950.

Rupprecht, C.E. et al. (1992) "Primate responses to a vaccinia=–rabies glycoprotein recombinant virus vaccine" Vaccine 10(6):368–374.

Small, P.A. Jr., G.L. Smith, B. Moss (1985) "Intranasal Vaccination iwth a Recombinant Vaccinia Virus Containing Influenza Hemagglutinin Prevents Both Influenza Virus Pneumonia and Nasal Infection: Intradermal Vaccination Prevents Only Viral Pneumonia" Vaccines 85:175–176.

Smith, G.L., B. Moss (1983) "Infectious poxvirus have capacity for at least 25,000 base pairs of foreign DNA" Gene 25:21–28.

Smith, G.L., B.R. Murphy, B. Moss (1983) "Construction and characterization of an infectious vaccinia virus recombinant that expresses the influenza hemagglutinin gene and induces resistance to influenza virus infection in hamsters" Proc. Natl. Acad. Sci. USA 80: 7155–7159.

(List continued on next page.)

Primary Examiner—Mary E. Mosher
Assistant Examiner—Ali R. Salimi
Attorney, Agent, or Firm—Saliwanchik, Lloyd & Saliwanchik

[57] ABSTRACT

The subject invention pertains to a novel recombinant vaccinia virus vaccine for use in immunizing animals and humans against disease. The vaccine comprises a live vaccinia or replication deficient mutant vaccinia virus capable of expressing a single or multiple heterologous genes or gene fragments. In a preferred embodiment, the recombinant virus is contained in an orally-administered package that will only dissolve in the host animal's gut. The subject invention also pertains to a method of inducing a broad protective immune response through the oral administration of the recombinant vaccinia virus.

12 Claims, 8 Drawing Sheets

OTHER PUBLICATIONS

Wells, M.A., F.A. Ennis, P. Albrecht (1981) "Recovery from a Viral Respiratory Infection II. Passive Transfer of Immune Spleen Cells to Mice with Influenza Pneumonia" The Journal of Immunology 126(3):1042–1046.

Wu, H.-Y., M.W. Russell (1993) "Induction of Mucosal Immunity by Intranasal Application of a Streptococcal Surface Protein Antigen with the Cholera Toxin B Subunit" Infection and Immunity 61(1):314–322.

Yap, K.L., G.L. Ada, I.F.C. McKenzie (1978) "Transfer of specific cytotoxic T lymphocytes protects mice inoculated with influenza virus" Nature 273:238–239.

Hagansee, M.E. et al. (1995) "Immunization of Mice with HPV Vaccinia Virus Recombinants Generates Serum IgG, IgM, and Mucosal IgA Antibodies" Virology 206:174–182.

Issekutz, T.B. (1984) "The Response of Gut–Associated T Lymphocytes to Intestinal Viral Immunization" The Journal of Immunology 133(6):2955–2960.

Sutter, G., B. Moss (1992) "Nonreplicating vaccinia vector efficiently expresses recombinant genes" Proc. Natl. Acad. Sci. USA 89:10847–10851.

Meyer, H., G. Sutter, A. Mayr (1991) "Mapping of deletions in the genome of the highly attenuated vaccinia virus MVA and their influence on virulence" Journal of General Virology 72:1031–1038.

Werner, G.T. et al. (1980) "Studies on Poxvirus Infections in Irradiated Animals" Archives of Virology 64:247–256.

Meitin, C.A. et al. (1994) "Enteric immunization of mice against influenza with recombinant vaccinia" Proc. Natl. Acad. Sci. USA 91:11187–11191.

ENTERICALLY ADMINISTERED RECOMBINANT POXVIRUS VACCINES

This is a continuation-in-part of application Ser. No. 08/330,641, filed Oct. 28, 1994, now abandoned.

BACKGROUND OF THE INVENTION

The subject invention described herein relates to the field of vaccines. Each year millions of children die of vaccine-preventable diseases. It is estimated that at least one child in five, including many of the children in the United States under the age of 2, has not been fully vaccinated (Gibbons, 1994). To help solve this problem, The Children's Vaccine Initiative proposed the development of a multivalent, heat-stable, inexpensive, orally-administered, safe and effective vaccine. Oral administration of vaccines may also help reduce children's fear of shots at the doctor's office.

A vaccine based on recombinant vaccinia virus meets many of these requirements. Vaccinia is a non-oncogenic virus that reproduces entirely within the cytoplasm of a host eukaryotic cell. Methods for inserting foreign DNA sequences into vaccinia are known in the art and at least 25 kb of heterologous DNA (representing about 10-20 genes) can be inserted into vaccinia virus genome (Smith et al., 1983). When administered parenterally, an immune response can be induced to the products of multiple heterologous genes expressed by a recombinant virus (Perkus et al., 1985). Lyophilized vaccinia virus is very heat-stable, maintaining infectivity after two hours at 100° C. (Arita, 1973). Vaccinia vaccine is also inexpensive, having been produced for about $0.03 to $0.04/per dose during the smallpox eradication program (Fenner et al., 1988). In addition, vaccinia virus can be readily grown in laboratory cultures and prepared in stable, freeze-dried forms.

Orally-administered liquid vaccinia/rabies recombinant vaccines have been used to successfully immunize animals in the wild (Blancou et al., 1986 and Rupprecht et al., 1986), probably as a result of viral replication in the tonsils (Rupprecht et al., 1988). However, there are several problems associated with oral administration of a liquid containing vaccinia or vaccinia recombinants. It can produce oral lesions (Greer et al., 1974 and Hochstein-Mintzel et al., 1972) and has been shown to be poorly immunogenic in chimpanzees when given orally (Rupprecht et al., 1992). In addition, the vaccinia virus is rapidly destroyed by stomach acid or bile (Hochstein-Mintzel et al., 1972), thereby eliminating intragastric immunization as a viable mode of administration.

The effectiveness of a particular vaccine may depend upon which cells or tissues of the immune system are activated by the vaccine. The role of three arms of the immune system, namely serum antibody, mucosal IgA antibody, and cytotoxic T-lymphocyte (CTL) activity, have been studied using an influenza viral challenge of mice. In this model, secretory IgA antibody has been shown to prevent infection of the nose (Renegar et al., 1991a; Renegar et al., 1991b), and serum IgG antibody has been shown to prevent infection of the lung (Loosli et al., 1953). When the virus evades these protective antibodies, anti-influenza CTL activity enhances recovery (Yap et al., 1978, Lin et at., 1981, and Wells et al., 1981).

Intradermal (scarification) administration of a recombinant vaccinia virus that expresses the influenza hemagglutinin protein (vac/H1) has been shown to induce both serum antibody that prevents viral pneumonia (Smith et al., 1983, Small et at., 1985, and Bennink et al., 1984) and CTL activity that promotes recovery (Bennink et al., 1984, Andrew et al., 1987, and Bender et al., 1990). However, this route of vaccine administration does not induce mucosal IgA antibody (Small et al., 1985 and Meitin et al., 1993). Intranasal, intradermal and enteric immunization of cotton rats with a live recombinant vaccinia virus expressing the respiratory syncytial virus F glycoprotein has also been reported (Kanesaki et al., 1991). Intranasal administration of vac/H1 recombinant virus induces serum IgG antibody, IgA antibody in nasal wash and CTL activity (Meitin et al., 1991); however, there are several practical limitations to this approach with humans. For example, storage constraints, temperature stability, and intranasal administration of liquids may pose practical problems in developing countries.

Thus, there remains a need for a vaccine that is temperature-stable, inexpensive, easily administered and which also induces serum IgG, mucosal IgA and cell-mediated immune responses. Such a recombinant vaccine should meet all the requirements of The Children's Vaccine Initiative and thereby greatly facilitate immunization, especially in developing countries.

BRIEF SUMMARY OF THE INVENTION

The subject invention concerns a novel recombinant vaccine composition for immunizing animals, including humans, against pathogenic disease organisms. Specifically, the vaccine comprises a live vaccinia, mutant vaccinia virus, such as a replication deficient or a highly attenuated vaccinia of which modified vaccinia virus Ankara (MVA) is a preferred virus, deletion or insertion mutants of vaccinia virus, or a canary pox virus, (each of which is referred to herein generally as "vaccinia" for ease of reference), that expresses a heterologous gene or genes. In a preferred embodiment, the recombinant virus is contained in an orally-administered, enteric-coated capsule or other suitable dosage form that will only dissolve and release virus when it reaches the host's small intestine. Once in the intestine, the recombinant virus induces a host immune response against the expression product of the heterologous genes. Advantageously, such an administration of the recombinant vaccine according to the subject invention is capable of inducing serum IgG, mucosal IgA and a cell-mediated immune response by the host animal. Thus, the vaccine of the subject invention is capable of providing multiple levels of immune protection against pathogenic infections in a form that is inexpensive, environmentally stable, easily administered, safe and effective.

The subject invention further concerns a method of inducing a protective immune response by immunization with an orally administered live recombinant vaccinia virus. The induced serum IgG, mucosal IgA and cell-mediated responses are directed against the heterologous gene product (s) expressed by the recombinant virus. The multi-level immune response induced by the subject vaccine coffers protective immunity on a host from targeted pathogens.

In one embodiment of the subject invention, the enteric administration of a recombinant vaccinia virus that expresses the influenza hemagglutinin gene (this recombinant virus is referred to herein as vac/H1) induced mucosal IgA and serum IgG anti-H1 antibody, in addition to inducing CTL activity in mice. This immune response provided protection of both the nose and lungs of the mice from a subsequent vital challenge with influenza.

DETAILED DESCRIPTION OF THE PREFERRED EMBODIMENT

Figure 1A:
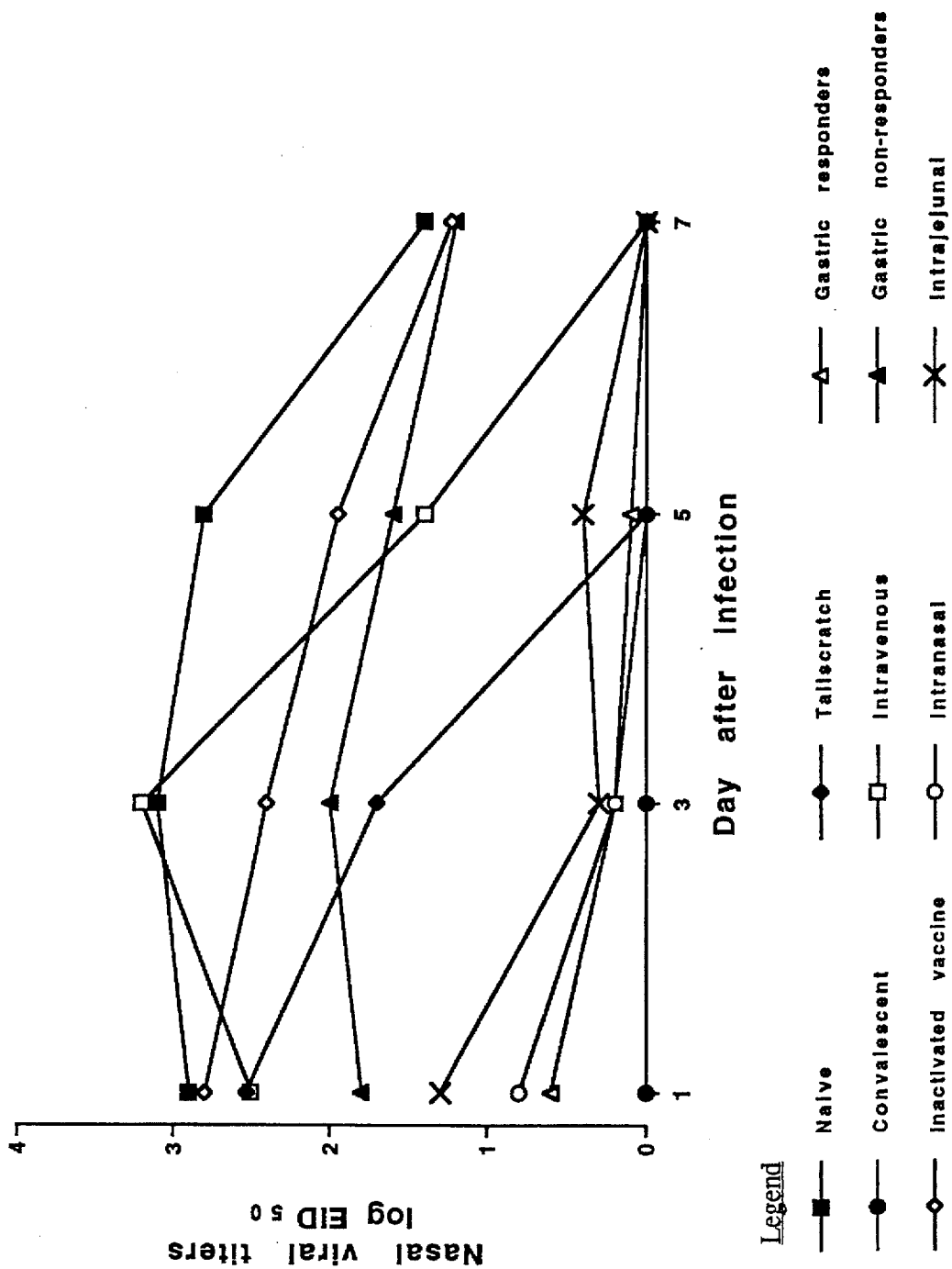
FIGS. 1A and 1B show influenza virus titers from the nose (FIG. 1A) and lungs (FIG. 1B) of research animals. Titers are reported as the $\log_{10}$ of the 50% egg infectious doses (log $EID_{50}$). All points represent the average of 6 animals except intragastric responders and intragastric-nonresponders: on days 1, 3, and 7, there were four animals in the responder group and two animals in the nonresponder group; on day 5 there were three animals in each group. Undetectable virus was defined as 0 on this log scale.

The subject invention concerns novel recombinant vaccinia, mutant vaccinia virus, such as a replication deficient or a highly attenuated vaccinia of which modified vaccinia virus Ankara (MVA) is a preferred virus, deletion or insertion mutants of vaccinia virus, or a canary pox virus, (each of which is referred to herein generally as "vaccinia" for ease of reference), compositions and methods of inducing a broad immune response in a host organism using this vaccine. Specifically, the subject invention concerns a live recombinant vaccinia virus that can express the products of one or more heterologous genes. When expressed by the vaccinia virus in a host animal these gene products induce a multi-component immune response in the host. The immune response includes serum IgG antibody, mucosal IgA antibody, and cell-mediated responses directed against the heterologous gene products. Thus, once vaccinated according to the subject invention, the host animal is either protected from infection or at least primed to mount a fully protective secondary immune response upon exposure to any pathogen expressing the heterologous gene products to which the host has been sensitized. Accordingly, the host animal vaccinated with the vaccine of the subject invention can be effectively immunized against a wide variety of pathogens including bacteria, viruses, fungi, and parasites.

In an exemplified embodiment, the live recombinant vaccinia virus is administered enterically to a host animal. In another embodiment, a mutant form of a recombinant vaccinia virus, such as a strain that is replication deficient in mammalian cells, can be used according to the subject invention. More preferably, the recombinant virus is orally administered in a form that releases the virus only in the intestine of the host animal. Techniques for preparing live vaccine in enterically-coated dosage forms are known in the art (see, for example, Stickl, A.H., British Patent No. 1-333-512). As referred to herein, the term "intestine" is meant to include both the large and small intestinal tracts. In a preferred embodiment, immunization with the subject vaccine occurs primarily in the small intestine.

Enteric administration of replication competent recombinant virus results in the exposure of IgA precursor B cells in lymphoid tissue of the intestine, such as Peyer's Patches, to the expressed heterologous gene products. These IgA precursor B cells can then migrate to mucosal tissues, such as the respiratory tract, where they may differentiate into mature IgA-secreting plasma cells. In addition, Ig secreting B cells in other lymphoid tissues, and various components of the cellular immune system, such as T cells and macrophage, are stimulated upon exposure to the heterologous gene products.

Preferably, the recombinant vaccinia virus of the subject invention contains multiple heterologous genes that encode polypeptide antigens which are expressed after introduction into the host system. A polyvalent vaccine according to the subject invention can be used to immunize a host animal against multiple diseases produced by a variety of pathogenic organisms. Similarly, such a polyvalent vaccine can be used to induce a broad immune response against a single type of pathogen, particularly those pathogens that express various forms of antigens or that express different antigens at different times during their life-cycle.

The recombinant vaccinia virus of the subject invention can be used with a variety of heterologous genes or gene fragments. For example, genes from pathogens that cause influenza, measles, hepatitis B, diphtheria, tetanus, mumps, rubella, and others, can be inserted into the recombinant vaccinia. The subject invention can be used with a wide variety of gene inserts. Thus, the subject invention can be used to prevent diseases, such as pertussis, tuberculosis, cholera, and immune deficiency conditions induced by infection, once appropriate gene inserts are identified. In addition, the subject invention can be readily used in other areas of vaccine technology, such as in cancer prevention or fertility control, once appropriate antigens are identified. The subject invention also contemplates the use of chimeric genes that express a fusion product comprising the expression products of a portion of two or more heterologous genes. The subject invention further contemplates the use of genes that encode protein structures that mimic polysaccharide antigens.

The subject invention can be used in vaccinating both animals and humans against pathogenic organisms. The vaccine can be administered in a manner compatible with the dosage formulation, and in such amount as will be therapeutically effective and immunogenic. The quantity to be administered can depend upon the subject to be treated, the immunogenicity of the expressed gene products, and the degree of protection desired. Dosage parameters can be readily determined by those skilled in the art using the disclosure provided herein.

As described herein, intrajejunal immunization with a recombinant vaccinia expressing the influenza hemagglutinin protein (vac/H1) in a influenza/mouse model system consistently induced nasal, gut, and vaginal wash IgA antibody as well as serum IgG antibody and CTL activity in the host mouse that was directed against the hemagglutinin. The nasal IgA antibody was responsible for a significant reduction in nasal virus following challenge of enterically immunized mice (Renegar et al, 1991a, b). The serum IgG antibody was responsible for a significant reduction in lung virus following challenge of immunized mice. Mice immunized intrajejunally multiple times with the recombinant vaccinia vac/H1 developed an immune response to the hemagglutinin in spite of having been immunized parenterally fifty-three days earlier with a wild-type (WR) strain of vaccinia.

To be of practical value, a vaccine must be safe for both the vaccinated person and that person's contacts. Mice immunized with the Vae/H1 recombinant showed no ill effects from enteric immunization. The mice had no change in bowel habits or ruffled fur. The enterically immunized mice did not shed vaccinia virus in their feces. However, if other species do excrete vaccinia virus, or if the vaccinia is potentially harmful to the animal, replication deficient mutant forms of vaccinia strains such as MVA (Sutter et al., 1994) or a canary pox virus (Cadoz et al., 1992) can be used.

There are two potential disadvantages with using recombinant vaccinia viruses as human vaccines. The first issue is safety. During the Smallpox Eradication Programme, serious adverse reactions from vaccinia occurred at a rate of 38/1,000,000 for eczema vaccinatum, 1.5/1,000,000 for progressive vaccinia, and 12/1,000,000 for post-vaccinial encephalitis. Bemuse of the risk of dissemination, vaccination was contra-indicated in infants with eczema or anyone suffering from immune dysfunction (Centers for Disease Control, 1991; Fenner, et al, 1988). These risks should be negligible with avian host restricted poxvirus such as canarypox (Cadoz et al., 1992) and replication deficient vaccinia virus such as and including modified vaccinia virus Ankara (MVA). MVA was derived prior to eradication of smallpox from repeated (over 570) passages of vaccinia virus Ankara in chicken embryo fibroblasts (Hochstein-Mintzel, et al., 1972). Genetic analysis revealed that MVA had suffered six major deletions of its genome, resulting in the loss of 30,000 base pairs (15% of its genome) so that it became host-restricted and unable to grow efficiently in mammalian cell lines (Meyer et al., 1991). The block in replication of MVA in human cells occurs at a step in virion assembly rather than at an early stage of infection as happens with some other poxvirus host-restricted mutants (Sutter et al., 1992). MVA was found to be avirulent in both normal and immunocompromised animals and was given to 120,000 people, many at high risk of complications from the standard vaccine, without significant side effects (Hochstein-Mintzel, et al., 1972, supra; Werner et al., 1980; Mayr, et al, 1978; Mayr et al., 1975, Mayr et al., 1979; Stickl et al., 1974). Further, recombinant gene expression is unimpaired (Sutter et al., 1992, supra). Mice injected intranasally, subcutaneously, intramuscularly or intravenously with a recombinant MVA that expresses the genes of influenza hemagglutinin (HA) and nucleoprotein (NP) developed anti-H1 serum IgG antibodies and CTL activity and were protected from a lethal challenge with a homologous influenza virus (Sutter et al, 1994). There was no evidence from this report relating to oral immunization using recombinant MVA, and induction of IgA is not demonstrated.

The second issue that lowered enthusiasm for vaccinia vectors was the demonstration that while parenteral immunization stimulated protective levels of serum IgG antibody and cellular immunity, it did not induce mucosal immunity (Small et al, 1985). We have demonstrated, however, that intragastric administration of a recombinant vaccinia virus induces solid mucosal, humoral, and cellular immunity. Moreover, vaccinia/rabies recombinants given as oral bait have successfully immunized animals in the wild, probably as a result of viral replication in the tonsils (Blancou et al., 1986; Rupprecht et al, 1986; Rupprecht et al., 1988).

Non-replicating or replication defective vectors can also include a gene for the expression of interleukin-2 in order to supplement the induced immune response (Flexner et al., 1987). Thus, oral administration of an enteric coated recombinant vaccinia or mutant forms of recombinant vaccinia can provide a safe and effective mode of immunization. The development of multivalent vaccinia recombinants makes the subject invention even more effective.

What is most surprising is that, according to the instant invention, a replication-deficient vital vector, exemplified herein by a recombinant MVA, is capable of inducing significant immune response which in appropriate animal models exhibit significant indicia of efficacy in man.

Our studies dearly demonstrate the potential immunogenicity and efficacy of MVA HA-NP as an oral vaccine. One dose of the vaccine induced low levels of both mucosal and serum antibodies. A second i.g. dose of MVA HA-NP significantly boosted the titer of anti-influenza serum antibody and, especially, mucosal IgA antibody showing that the first dose primed the mice for an anamnestic response. The biological effectiveness of these immunizations was shown in a series of challenge experiments. The mice that received one i.g. dose of MVA HA-NP were partially protected from a homotypic challenge and all of those that received two doses were fully protected from pulmonary infection. Most (10 to 17 mice) were also protected from nasal infection. One i.g. dose of MVA HA-NP completely protected the lungs, but not the noses. These data serve to emphasize the importance of mucosal versus serum antibodies in the prevention of infection of the upper and lower respiratory tract, respectively (Renegar et al., 1991a; Renegar et a/L, 1991b; Barber et a/L, 1978; Clements et al., 1986).

Recovery was evaluated and demonstrated herein by data generated in experiments with heterologous, H3N2 influenza virus. These showed that viral clearance of both the lung and the nose was enhanced with i.g. MVA HA-NP, while i.m. MVA HA-NP enhanced recovery of only the lungs (FIG. 4). Based on previous studies, this was most likely due to induction of anti-NP CTL activity, but other factors may be involved. For example, we recently showed that heterotypic immunity can be induced in β2m-/-mice; the mechanism of this protection did not involve class I major histocompatibility complex (MHC)-restricted T cells, but may have been due to induction of class II MHC-restricted CD4+T cells or induction of mucosal IgA (Bender et al., 1994; Mazanec et al., 1992; Mazanec at al., 1995). Regardless of the mechanism of the enhanced recovery these experiments highlight the importance of using a conserved protein such as NP (Gammelin et al., 1991) in a vaccine in order to generate a heterotypic protective response.

Oral immunization with replication-deficient recombinant vaccinia virus such as MVA offers many advantages over other vaccine candidates. First, as demonstrated here, this method is not only effective in inducing immune response in all three arms of the immune system-serum antibody, mucosal IgA antibody, and cell-mediated immunity-it is also efficacious. Use of an oral rather than a parenteral vaccine may enhance patient (and/or parental) acceptance and would obviate the need for syringes and needles. Second, MVA is an extremely safe vector that has undergone extensive safety testing in humans and animals (Hochstein-Mintzel, et al., 1972; Werner et al., 1980; Mayr, et al., 1978; Mayr et al., 1975, Mayr et al., 1979; Stickl et al., 1974; Meitin et al., 1991). Third, multivalent recombinant MVA can be constructed. Even if it proves to be too difficult to transfer more than a few genes into MVA or have them expressed in appropriate concentrations, a cocktail of recombinant MVA viruses, each containing several genes, would be expected to work based on the instant disclosure. Fourth, lyophilized vaccinia is extremely heat-stable. Heating to 100° C. for two hours lead to a loss of only one log of infectivity. After storage at 45° C. for two years, it was still 100% successful in vaccination of volunteers (Cross, 1957). These properties make oral recombinant MVA an ideal candidate vaccine to meet all the requirements of the Children's Vaccine Initiative (World Bank, 1993; Bloom, 1989; Robbins et at., 1988). It could provide children in the developing world with an ideal vaccine and save children throughout the developed world from the fear of shots.

From the foregoing description, it should be apparent that success in using an MVA recombinant for oral immunization could not have been predicted. In contrast to parenteral injection with replication competent or replication deficient viruses, wherein the virus can directly reach cells of the immune system, a replication deficient vaccinia or pox virus introduced into the gut would not be expected to directly reach cells of the immune system. Therefore, a prior, it was not known whether immunization with a replication defective vaccinia or pox virus, via the small intestine would be effective. This is because access to immune responsive cells in the intestine is severely restricted, with the likely outcome of such a mode of immunization would be abortive infection of intestinal epithelium. Even having demonstrated the effectiveness of this method herein, the mechanism is unknown, although it is postulated that the M-cells covering Peyer's patches in the gut may play a role. In addition, in one embodiment of this invention, particular technical advances have been made which contribute to the success of an oral MVA based vaccine. In particular, the evidence adduced herein of efficacy of the oral vaccine is extremely significant and novel. In addition, we have pre-treated the animal models with an acid release blocker (cimetidine, but any like agent, such as PEPCID may be used) to prevent destruction of the oral vaccine en-route to the intestine. In addition, we pre-treated the animals with an active analog of the cholecystokinin hormone to ensure that bile wold not be available to destroy the vaccine. Either or both of these pre-treatments, or modifications thereof may be used with enteric coated virus.

In humans, both of these pre-treatments may be acceptable. However, in terms of the bile secretions, pre-treatment with a cholecystokinin antagonist such as are well known in the art, may be more clinically acceptable. This pre-treatment would ensure that bile is not released when the vaccine is en-route. These pre-treatments may be less important with an efficiently enteric-coated vaccine, but may be of assistance. For the purposes of the present studies, these pre-treatments provided for efficient oral immunization.

Materials and Methods

Unless indicated otherwise, the following materials and methods were used.

Immunization of animals. Female BALB/e mice, 6–8 weeks old were given a single immunization either by scarification of the tail, intravenous, intranasal, intragastric, or intrajejunal administration of $10^8$ pfu of a vaccinia-influenza recombinant containing the hemagglutinin gene from H1N1 PR8 influenza (this recombinant is referred to herein as vac/H1) which was constructed as previously described (Flexner et al., 1987). All mice were fasted overnight before immunization. Intragastric administration was accomplished by use of an oral gastric tube. Intrajejunal administration was done by injection during laparotomy. Animals were anesthetized with 0.1–0.2 ml of sodium pentobarbital (0.09 g/ml) and the peritoneal cavity was entered. The stomach and small bowel were identified and the vaccine was placed into the lumen of the jejunum with a 26 gauge needle. The incision was then closed. The three control groups consisted of naive mice, mice injected intraperitoneally (i.p.) two times with inactivated H1N1 influenza vaccine, and mice infected intranasally while awake with live HIN1 PR8 influenza virus.

Six weeks following inoculation, the mice were sacrificed. Splenic lymphocytes were collected for measurement of anti-influenza cytotoxic T lymphocyte (CTL) activity. Serum, nasal wash (Renegar et at., 1991b), gut wash, and vaginal wash (Wu et al., 1993) were collected for anti-influenza antibody determination. These were later assayed by ELISA for serum IgG as well as nasal and gut wash IgA anti-influenza antibody, and the liters were then calculated by comparison with monoclonal controls (Meitin et al., 1991). Data were analyzed using a one factor ANOVA. Student-Newman-Keuls post hoc test was used to analyze differences between groups.

Cytotoxic T Lymphocyte Assay. Spleens were obtained from BALB/c (H-$2^d$) mice 6–8 weeks post-intrajejunal immunization with $10^8$ pfu of vac/H1. Spleens were also obtained from H1N1-infected mice, wild-type vaccinia-immunized mice, and naive mice. Spleen cells were then cultured for seven days with H1N1-sensitized autologons splenocytes and then tested in a 6 hr $^{51}$Cr release assay against vac/H1-, vaccinia containing the nucleoprotein gene (vac/NP-), or H1N 1-sensitized P815 (H-2$^d$) mastocytoma cells (Bender et al., 1991). Percent (%) specific lysis was determined as: (experimental release-spontaneous release/total release-spontaneous release)×100. Multiplicity of infection was 100 pfu per cell for vaccinia targets and 10 TCID$_{50}$ per cell for H1N1 targets. Spontaneous release was less than 15% for all groups. The effector cell/target cell ratio was 30:1.

Following are examples which illustrate procedures, including the best mode, for practicing the invention. These examples should not be construed as limiting. All percentages are by weight and all solvent mixture proportions are by volume unless otherwise noted.

EXAMPLE 1

Induction of Anti-H1 Antibody

Mice were immunized as described in the methods section above and tested for the presence of IgG and IgA antibodies to H1. Tilers of detected antibodies from each immunization group are shown in Table 1. Naive mice had no detectable anti-H1 antibody. Convalescent mice developed high levels of serum IgG, nasal IgA, and gut IgA anti-H1 antibody. Control mice immunized intraperitoneally with inactivated vaccine developed the highest liters of anti-influenza serum IgG antibody. Mice immunized with the vac/H1 recombinant by either scarification or intravenous injection developed high titers of anti-influenza serum IgG antibody, similar to those seen in convalescent mice, although not quite as high as seen in mice immunized with standard vaccine. Mice immunized intranasally and intrajejunally developed lower but readily detectable levels of serum IgG antibody. Intragastric immunization produced inconsistent results: four of six mice responded similarly to the intranasal and intrajejunal groups, but two were unresponsive.

Significant levels of mucosal (nasal wash and gut wash) IgA were induced only by influenza virus infection or by vac/H1 given by a mucosal route, i.e., into the nose, stomach, or jejunum. Intranasal, intrajejunal, and intragastric (four of six) immunized mice all had nasal wash liters similar to those of convalescent mice. Intrajejanal immunization produced gut wash liters similar to those of convalescent mice and higher than those of the intranasal or responding intragastric immunized mice. The administration of cimetidine, a drug that inhibits gastric acid secretion, did not increase the percentage of mice that responded to intragastric immunization. Neither parenteral route of immunization with vac/H1 (scarification or i.v.) nor i.p. immunization with the standard vaccine stimulated significant liters of mucosal IgA antibody (nasal wash IgA anti-H1 titers of 0.04, <0.01 and 4 respectively).

TABLE 1

Anti-H1 influenza antibody titers by ELISA

| GROUP | Serum IgG (× 10$^{-3}$) | Nasal Wash IgA (× 10$^{-5}$) | Gut Wash IgA (× 10$^{-5}$) |
| --- | --- | --- | --- |
| Naive | <0.1±0.06 | <0.01±0.01 | <0.01±0.01 |
| Convalescent | 212 ± 63 | 27 ± 6 | 18 ± 5 |
| Standard | 406 ±159 | 4 ± 2 | 2 ± 1 |

TABLE 1-continued

Anti-H1 influenza antibody titers by ELISA

| GROUP | Serum IgG (× 10$^{-3}$) | Nasal Wash IgA (× 10$^{-5}$) | Gut Wash IgA (× 10$^{-5}$) |
| --- | --- | --- | --- |
| vaccine - IP vac/H1 - scarification[1] | 123 ± 32 | 0.07±0.06 | 0.2 ±0.06 |
| vac/H1 - IV | 187 ± 38 | <0.01±0.01 | <0.01±0.01 |
| vac/H1 - intranasal | 24 ± 7 | 36 ± 11 | 12 ± 4 |
| vac/H1 - intrajejunal | 22 ± 1 | 27 ± 7 | 19 ± 3 |
| vac/H1 - intragastric responders (n = 4)[2] | 21 ± 6 | 25 ± 8 | 15 ± 3 |
| vac/H1 - intragastric nonresponders (n = 2) | <0.01±0.01 | <0.01±0.001 | <0.01±0.001 |

[1] Two of six mice tailscratched with the vac/H1 developed low titers of both nasal and gut wash IgA. This is most likely due to auto- or cross-immunization from grooming (Meitin et al., 1993).
[2] Mice that were immunized by the intragastric route were divided into two groups. One group (n = 4) had similar serum IgG and mucosal IgA antibody titers to those seen with intranasal and intrajejunal immunization, while the second group (n = 2) failed to develop any detectable anti-influenza antibody (<0.01 × 10$^{-3}$). (Statistically significant differences were not seen due to the low numbers of animals in the subdivided intragastric groups, i.e., 4 and 2.)

EXAMPLE 2

Induction of IgA Antibody and Cell-Mediated Immune Response

In a separate experiment, mice were immunized by either the intrajejunal or intragastric route described in the methods section. Six weeks later, vaginal wash fluid was obtained (Wu et al., 1993). No detectable IgA anti-H1 antibody was present in the vaginal wash of naive mice. Intrajejunal immunization was significantly more successful than intragastric in inducing vaginal anti-H1 IgA antibody; 14/17 (82%) of mice vaccinated intrajejunally had detectable IgA (titer of 14 responding animals=0.04×10$^{-5}$±0.03×10$^{-5}$), compared to 13/30 (43%) (p<0.05, two-tailed Fisher's exact test) vaccinated intragastrically (titer of 13 responding animals =0.10×10$^{-5}$±0.05×10$^{-5}$). This confirms that immunization of one mucosal surface will lead to immunization of others.

Memory CTL activity was determined for six of the intrajejunally immunized mice in two separate experiments as shown in Table 2. Mice immunized with wild-type vaccinia or naive mice had minimal activity. Mice convalescent from an influenza H1N1 infection yielded 32% lysis against vac/H1-sensitized targets, 49% against vaccinia containing the nucleoprotein gene (vac/NP)-sensitized targets, and 24% of lysis against H1N1-sensitized targets in the first experiment and 58% lysis against vac/H1 targets and 45% against vac/NP targets in the second experiment.

The mice immunized intrajejunally with vac/H1 had 32% lysis against vac/H1-sensitized targets, 11% lysis against vac/NP-sensitized targets, and 18% against H1N1-sensitized targets in the first experiment and 42% lysis against vac/H1 and 16% lysis against vac/NP in the second experiment. In another separate experiment, lysis of H3N2-sensitized P815 cells by splenocytes from vac/H1-immunized mice was less than 25% compared to 86% for lysis from a H1N1-infected mouse. Thus, most of the CTL activity was directed against the hemagglutinin and not to the vaccinia. The low anti-vaccinia CTL activity was undoubtedly due to the secondary in vitro stimulation with H1N1-sensitized stimulator cells rather than vaccinia-sensitized stimulator cells.

TABLE 2

Memory CTL activity induced by intrajejunal immunization with vac/H1.

| | | Mean % specific lysis of P815 cells sensitized with: | | |
|---|---|---|---|---|
| Experiment | Group | vac/H1 | vac/NP | H1N1 |
| #1 | Wild-type Vaccinia | 3 | 7 | 9 |
| | H1N1-infected | 32 | 49 | 24 |
| | vac/H1-intrajejunal | 32 | 11 | 18 |
| #2 | Naive | 1 | 1 | n.d. |
| | H1N1-infected | 58 | 45 | n.d. |
| | vac/H1-intrajejunal | 42 | 16 | n.d. |

EXAMPLE 3

Influenza Virus Challenge

In a third experiment, groups of mice that were immunized as described in the methods section above were challenged six weeks later with 20MID$_{50}$ of live influenza A PR8 (H1N1) administered intranasally while anesthetized (Yetter et al., 1980). Mice were sacrificed 1, 3, 5, and 7 days after challenge and virus titers determined for nasal and lung tissues (FIG. 1). The mice convalescent from a previous influenza infection had no virus in their noses. Naive mice had high titers of virus in their noses throughout the 7 days. Significantly lower levels of nasal virus were found in the three groups receiving successful mucosal immunization, i.e., vac/H1 intranasal, vac/H1 intrajejunal, and vac/H1 intragastric responders. Four groups of mice (those immunized by standard vaccine i.p., vac/H1 scarification, vat/H1 i.v., and vat/H1 intragastric nonresponders) had Day 1 nasal virus titers that were statistically indistinguishable from naive mice. Viral clearance after Day 1 was more rapid in mice that had received vac/H1 than either the naive mice, the non-responders, or those given standard vaccine i.p. Because respiratory viruses are primarily cleared by cytoxic T-cells, this more rapid clearance is most likely due to the higher levels of anti-influenza CTL activity induced by vac/H1 than by standard vaccine (Bender et al., 1990).

Figure 1B:
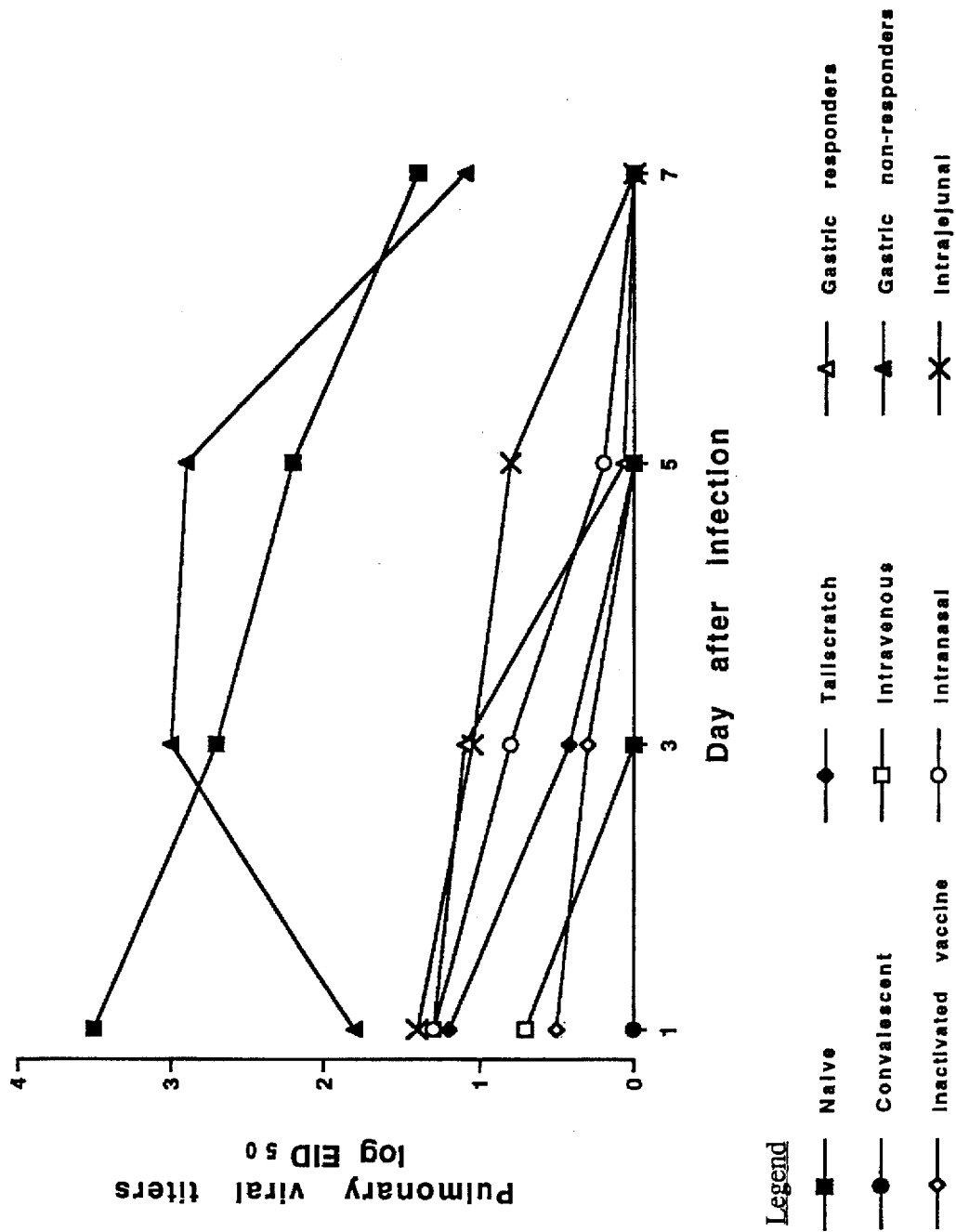

Virus titers in the lungs are also shown in FIG. 1A and 1B. Convalescent mice were solidly immune as evidenced by the lack of virus. Naive mice had high titers of virus throughout the seven days studied. The gastric non-responders were not statistically different from the naive mice in regard to virus shedding. All the remaining groups had statistically significantly (p<0.05) lower amounts of virus than the naive controls.

The variability in the amount of virus recovered from the intragastrically immunized mice (FIG. 1A and 1B) was similar to that seen in the intragastric group studied for antibody titer (Table 1). Fifteen of the 24 mice (62%) had reduced amounts of virus in the lungs and nose. The pattern was similar to that seen with other mucosally immunized animals. Mean serum IgG and gut wash IgA anti-influenza antibody titers measured in these same fifteen animals were 27 and 26 respectively, i.e., an antibody titer similar to other mucosally immunized animals. The lung and nasal virus shedding patterns of the remaining nine mice were similar to previously uninfected controls, and these mice had no detectable serum IgG or gut wash IgA antibody.

EXAMPLE 4

Vaccination Against HIV Infection

Live recombinant vaccinia virus is prepared containing heterologous DNA sequences that encode various HIV antigens. For example, the HIV gene sequences can include those that encode GP160, GP120, or subunits of these or other HIV proteins. The live recombinants are then prepared in an enterically-coated dosage form. The host animal or human ingests the vaccine which dissolves upon reaching the host's intestine. In the intestine, the free virus replicates and induces a host immune response against the HIV expression products. Subsequent administrations of vaccine can be determined and administered when necessary.

EXAMPLE 5

Vaccination Against Hepatitis B

Live recombinant vaccinia virus is prepared containing heterologous DNA sequences that encode hepatitis B antigens. The live recombinants are then prepared in an enterically-coated dosage form. The animal or human to be vaccinated orally ingests the vaccine preparation, which dissolves upon reaching the host's intestine and releases free virus. In the intestine, the free recombinant virus replicates and induces a host immune response against the hepatitis B surface antigen expression products of the heterologous genes. Upon subsequent exposure to hepatitis B virus, the immunized host can produce a strong, multi-level immune response against hepatitis B which protects the host from infection with the virus. Optimal dosage levels and subsequent administration of the recombinant vaccine can be determined by those skilled in the art.

EXAMPLE 6

Female BAlb/c mice were immunized intragastrically (i.g.) with MVA HA-NP one hour after co-administration of cimetidine to inhibit gastric acid secretion and cholecystokinin to induce emptying of the gallbladder prior to vaccine administration. Positive control mice were convalescent from an H1N1 (influenza A/PR/8/34) infection or given MVA HA-NP i.m. Negative control mice were naive animals or mice given wild-type MVA i.m.

Female BALB/c mice, 5–6 weeks of age (Taconic Laboratories, Germantown, N.Y.), were housed in specific pathogen free conditions. One hour before i.g. inoculations, each mouse received a combination of 3 mg of cimetidine HCl (SmithKline Beecham, Philadelphia, Pa.) and 0.02 µg of sincalide (the C-terminal octapeptide of cholecystokinin) (Squibb, Priceton, N.J.) in 100 µl ofPBS i.p. Mice received 200 µl of MVA HA-NP in 50 mM HEPES buffer (Mediatech, Washington, D.C.) containing $10^8$ p.f.u. via a 1" (2.5 era) feeding needle. In some mice, i.g. inoculation was repeated five weeks later. For i.m. inoculations, 100 gl of wild-type MVA or MVA HA-NP, containing $0.5×10^8$ p.f.u., was injected into each quadriceps muscle. Stock influenza viruses used for i.n. inoculation or challenge were grown in the allantoic cavity of 10-day old embryonated chicken eggs for 3 days at 35° C., harvested, and clarified. Virus stocks were titerd on Madin-Darby canine kidney cells (Bender, 1992). Mice used as convalescent controls were infected i.n. with 20 µl of influenza A/Puerto Rico/8/34 (H1N1) containing $10^{7.1}$ TCID$_{50}$. For challenge studies at nine weeks post initial immunization, mice were anesthetized with sodium pentobarbital and inoculated i.n. with H1N1.

Figure 2A:
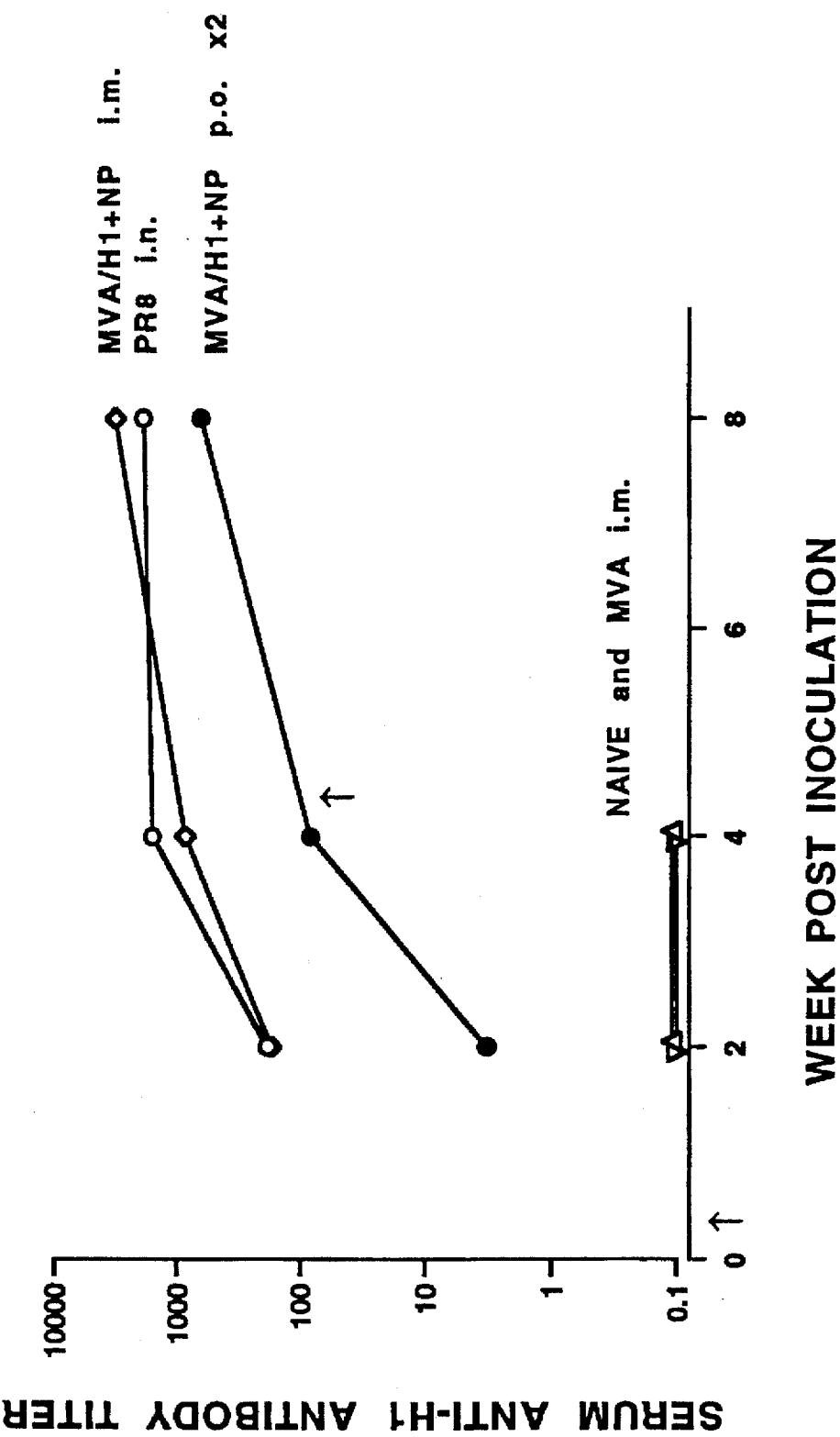
FIGS. 2A and 2B shows the induction of anti-H1 influenza virus specific serum antibodies by various vaccines or control. Mice were given $10^8$ pfu of MVA HA-NP by two intragastric (i.g.) inoculations (●). Control mice were inoculated intranasally (i.n.) with influenza A/Puerto Rico/8/34 (◇); i.m. with MVA (△) or MVA HA-NP (○); or were naive (□). Serum was obtain from tail vein and vaginal wash fluid was obtained by flushing the vagina 6–8 times with the same 80 µl of PBS (Meitin, et al., 1994) during weeks 2, 4, and 8. The ELISA to measure anti-H1 serum antibodies was performed as previously described (Meitin et al., 1991) and are plotted as X $10^{-1}$ (FIG. 2). Vaginal wash samples were frozen at –20° C. and later tested in an ELISA for anti-H1 IgA antibodies (FIG. 2B). To dissolve mucous strands, an equal quantity of 0.01M dithiothreitol (Sigma, St. Louis, Mo.) was added and the samples vortexed, incubated at room temperature for 30 minutes, and centrifuged for one minute at 15,000× g. Duplicate two-fold dilutions of samples were run in wells precoated with influenza hemagglutinin and in wells not containing antigen followed by goat anti-mouse igA (Sigma). The labelling reagent was alkaline phosphatase linked to rabbit anti-goat IgG (ICN Immunobiologicals, Irvine, Calif.) and p-nitrophenyl phosphate (Sigma) was used as substrate. Color was allowed to develop at 45 minutes at room temperature and absorbance at 405 nm was read on a Titertek Multiscan (Flow). Titers are expressed as the highest dilution for which the OD of the positive (antigen-containing) well divided by the OD of the respective negative (control) well gave a ratio greater than or equal to 2. The results are plotted as the geometric mean titer of the ELISA values (n=5–6/group) versus time after the first inoculation.
Figure 2B:
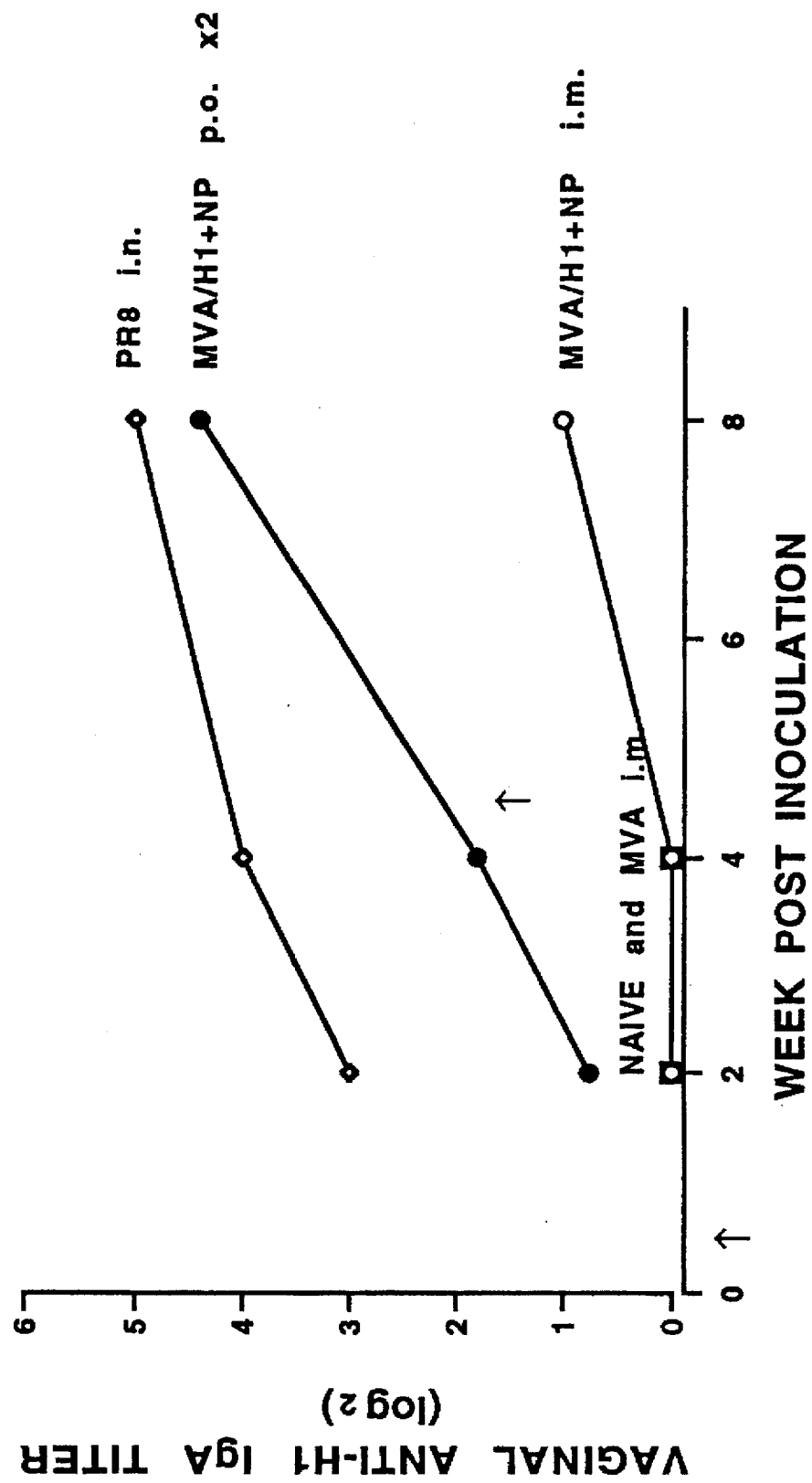

Oral vaccination was repeated in some of the animals five weeks later. Serum anti-H1 antibody was found in all mice receiving MVA HA-NP (either i.m. or i.g.) or H1N1 influenza virus (FIG. 2A), though levels were lower in the i.g. immunized mice. Mucosal anti-H1 IgA antibody was detected in the vaginal secretions of 31 of 33 mice that received MVA HA-NP i.g. and in 9 of 9 positive controls convalescent from an H1N1 infection. At 8 weeks, vaginal IgA anti-H1 titers of mice which received two does of MVA HA-NP were about half the titer of mice convalescent from influenza (FIG. 2B). The specific site of induction of mucosal IgA antibodies is unknown but may due to abortive infection of the epithelial cells of the small intestine with MVA HA-NP. Direct surgical implantation of a replicating recombinant vaccinia virus into the jejunum was more immunogenic than i.g. administration (Meitin, 1994, supra) probably because bile and gastric acid can inactivate vaccinia virus (Meitin, 1991, supra). We determined the effect of pretreatment of mice with cimetidine and cholecystokinin and found that this pretreatment enhanced the proportion of animals responding to i.g. administration of MVA HA-NP from $\approx 60\%$ to $\approx 100\%$. The appearance of anti-influenza IgA in vaginal and nasal wash following i.g. administration is consistent with the induction of the immune response in the intestine and migration of the immunocytes to other mucosal sites, a phenomenon recognized as pan of the common mucosal immune system (McGhee et al, 1990; McGhee et al., 1992; Brandtzeag, 1989).

EXAMPLE 7

Figure 3A:
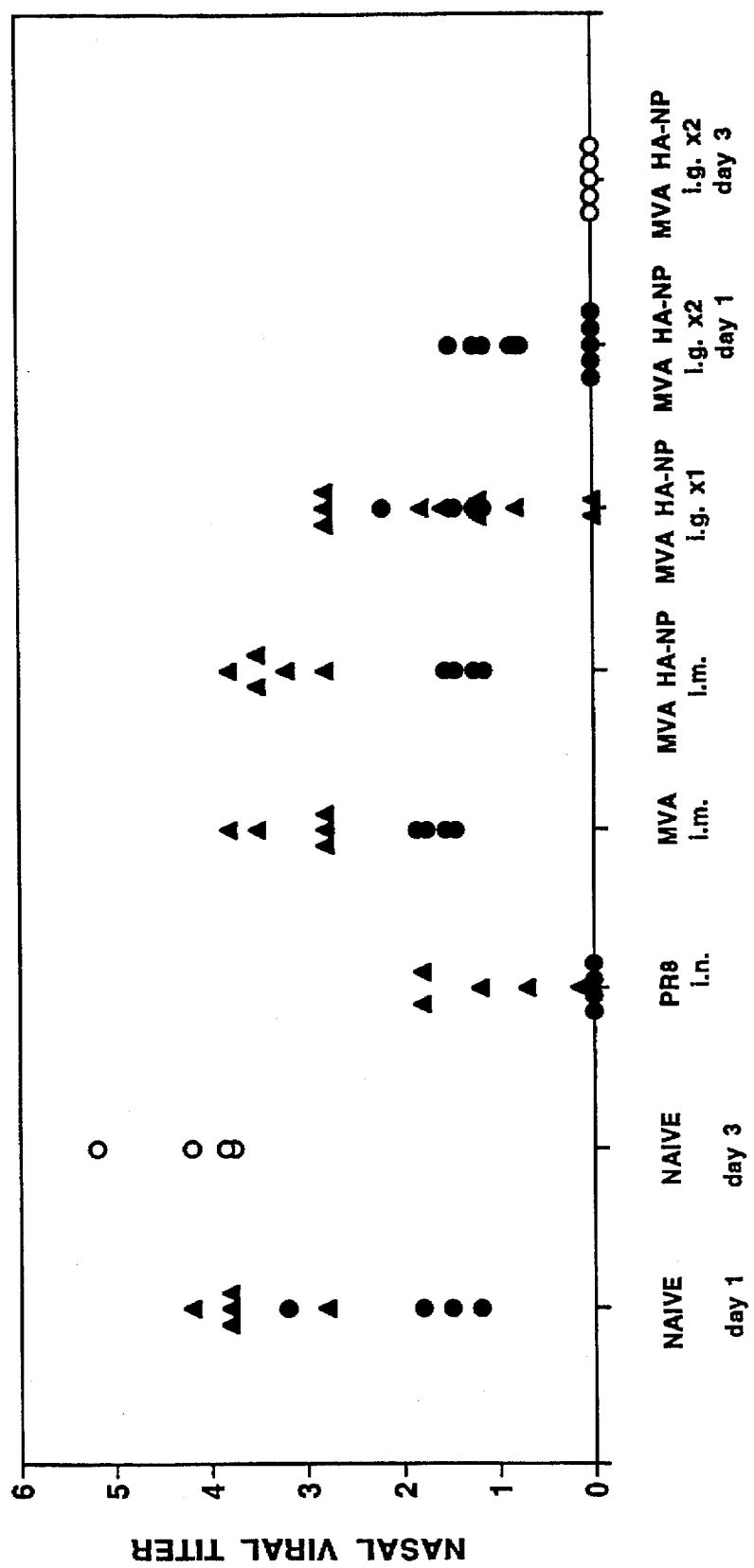
FIG. 3A and 3B shows nasal (A) and pulmonary (B) influenza virus titers in vivo following virulent homologous influenza virus challenge of animals pretreated with various vaccines or control. Twenty four days after the second inoculation with MVA HA-NP, mice were challenged with H1N1 and sacrificed one (closed symbols) and three (open symbols) days later. The data are a summary of two experiments challenging mice with using $10^{7.0}$ $TCID_{50}$ (▲) and $10^{4.1}$ $TCID_{50}$ (●, ○) of influenza virus. Virus titers were virtually identical to naive or i.m. MVA mice and are not shown. Day one nasal viral titers were significantly lower than those of control mice (naive and MVA i.m.) for MVA HA-NP i.g. (P<0.001, Exp. #1; p<0.05, Exp. #2) and H1N1 recovered (p<0.001, Exp. #1; p<0.05, Exp. #2), but not for MVA HA-NP i.m. (p>0.05, Exp. #1 and #2). Day one pulmonary viral titers were significantly lower than control for MVA HA-NP i.g. (p<0.001, Exp. #1 and #2), H1N1 recovered (p<0.001, Exp. #1 and #2), and MVA HA-NP i.m. (p<0.001, Exp. #1 and #2). Data were analyzed using InStat 2.00 (GraphPadSoftware, San Diego, Calif.) and a Power Macintosh 6100/66 computer. A one way ANOVA was followed by Student-Newman-Keuls multiple comparisons test.
Figure 3B:
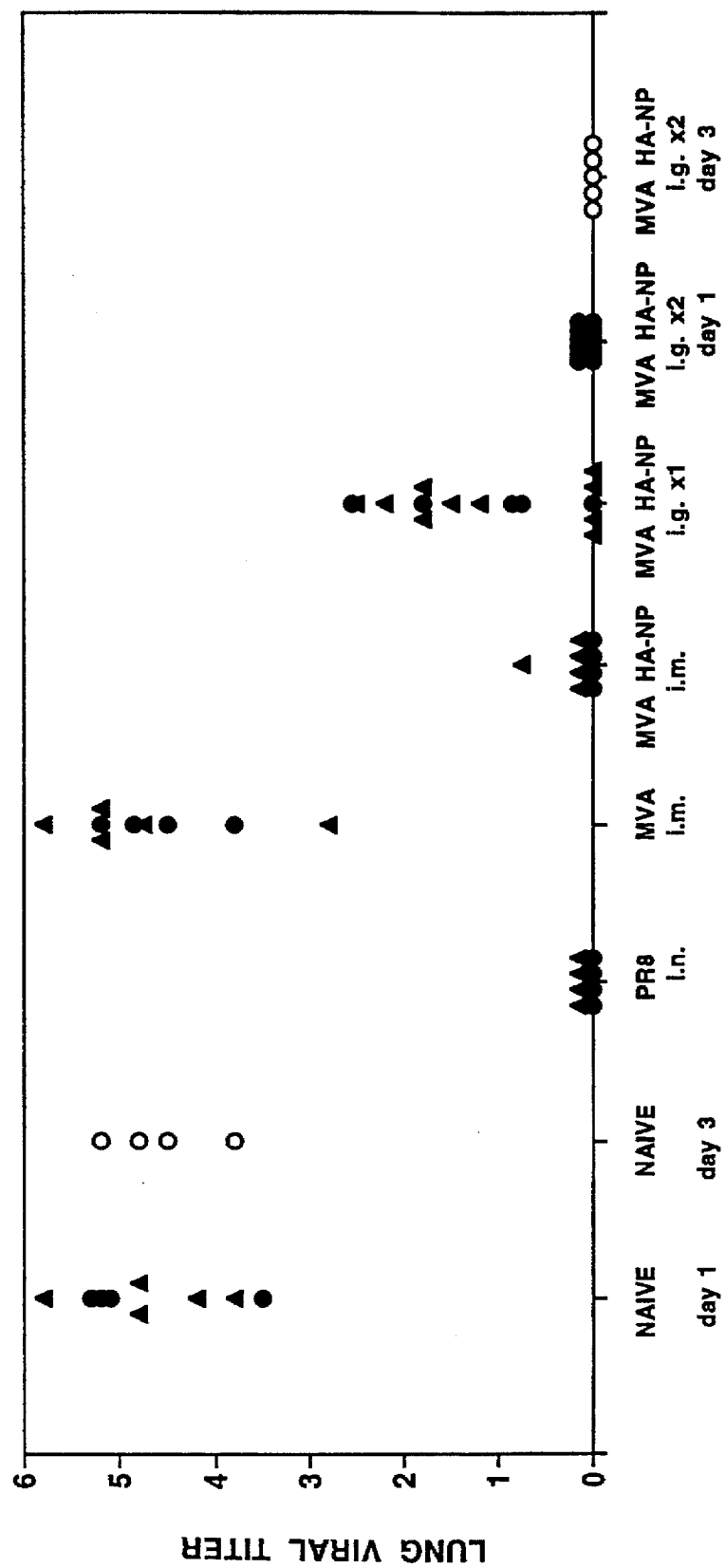

To evaluate the functional significance of the antibodies induced according to Example 6, vaccinated mice with a wide range of antibody titers were chosen for challenge with H1N1 influenza virus. Following this challenge, influenza virus reached a peak liter on day 3 post challenge of $\approx 10^4$ TCID$^{50}$ in the noses of naive healthy mice (FIG. 3A). The noses were protected best in those mice receiving two i.g. doses of MVA HA-NP (FIG. 3A). Five of the 12 mice receiving two i.g. doses of MVA HA-NP shed no virus from their noses on day 1 post-challenge and the mean titer of the total group (0.65±0.2) was significantly lower than naive (1.9±0.4), MVA HA-NP i.m. (1.4±0.1), or MVA i.m. (1.6±0.1) mice. All five mice immunized twice with MVA HA-NP i.g. that were sacrificed three days post challenge had high pre-challenge vaginal IgA antibody titers and shed no virus from their noses. Protection of the MVA HA-NP i.g.-immunized mice correlated strongly with vaginal wash anti-HA titer; 6 of 6 mice with a titer $\leq 1/8$ shed virus as compared to 1 of 11 mice with a titer $\geq 1/16$ (p=0.0004, Fisher's). As expected from the low anti-H1 IgA titers induced by one i.g. dose of MVA HA-NP, the noses of these mice were not protected from H1N1 challenge (1.5±0.2). Pulmonary virus shedding peaked at $\approx 10^5$ TCID$_{50}$ on day 1 post-challenge (FIG. 3B). Two i.g. doses of MVA HA-NP completely protected the lungs of 12 of 12 mice on the day following the challenge (FIG. 3B) as did MVA HA-NP i.m. in 4 of 4 mice. One i.g. dose provided partial, but significant, protection on day one following challenge (1.2±0.4; mean±SE) as compared to naive (4.8±0.4) or MVA i.m. (4.6±0.3) mice.

EXAMPLE 8

Figure 4A:
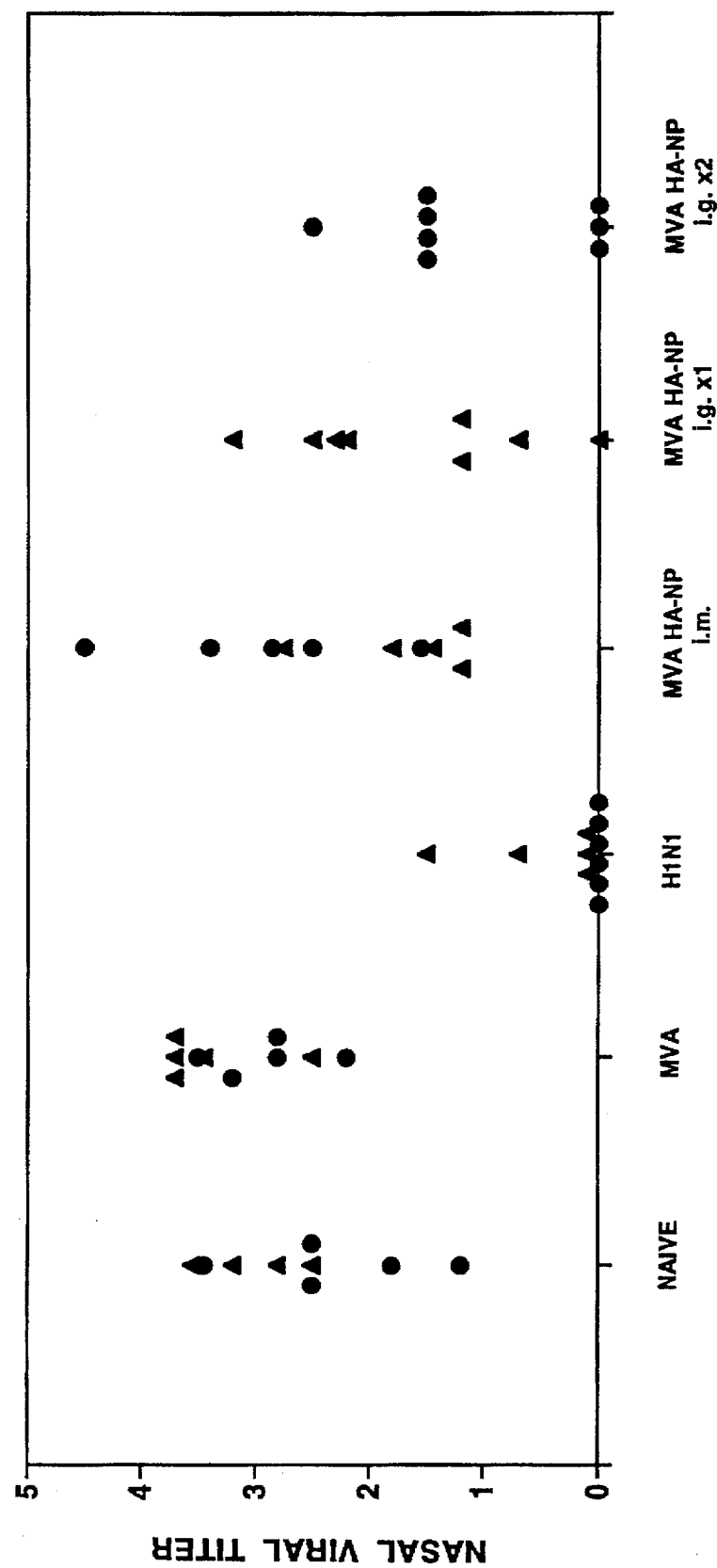
FIG. 4A and 4B shows mean nasal (A) and pulmonary (B) viral titer in vivo 5 days following virulent heterologous influenza virus H3N2 challenge of animals pre-treated with various vaccines or control. Four weeks after the second inoculation with MVA HA-NP, mice were challenged with H3N2 and sacrificed one and five days later. Day one titers (not shown) varied from 1.8 to 2.5 $TCID_{50}$ in the nose and 3.0 to 3.6 $TCID_{50}$ in the lungs and were not significantly different between groups. The data are a combination of two separate experiments using $10^{6.5}$ (▲) and $10^{4.6}$ (○) $TCID_{50}$ as challenge inoculation. Day 5 nasal viral titers were significantly lower than control (naive and MVA i.m.) for MVA HA-NP i.g. (p<0.05, Exp. #1 and #2) and H1N1 recovered (p<0.01, Exp. #1 and #2), but not MVA HA-NP i.m. (p>0.05, Exp. #1 and #2). Day 5 pulmonary viral tiers were significantly lower than control for MVA HA-NP i.g. (p<0.05, Exp. #1 and #2 X1 or X2 or both), H1N1 recovered (p<0.001, Exp #1 and #2), and MVA HA-NP i.m. (p<0.05, Exp. #1 p<0.05, Exp. #2).
Figure 4B:
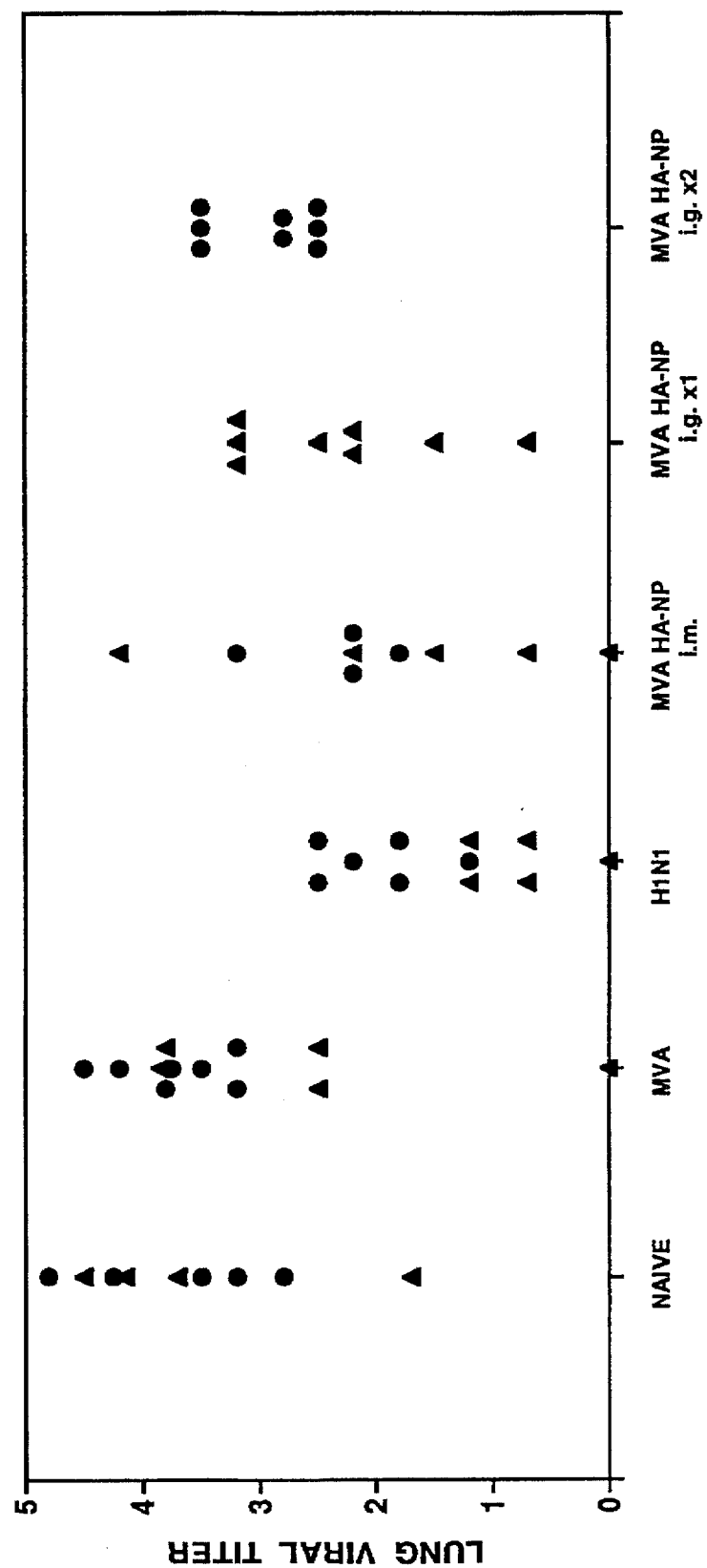

For determination of anti-influenza CTL activity, spleen were removed and cultured/n vitro with H3N2-infected autologous splenocytes for 7 days and cytotoxicity was assayed against H3N2-sensitized P815 cells (Bender et al., 1991, Bender et al., 1993). Table 3 demonstrates that two i.g. doses of MVA HA-NP induced lower levels of anti-influenza CYL activity than did nasal H1N1 influenza virus. As a measure of the efficacy of this cell-mediated immune response, MVA HA-NP immunized mice were challenged with influenza A/Port Chalmers/1/73 (H3N2). As these mice did not have protective antibodies, initial (day 1) virus titers of the nose and lung were statistically indistinguishable in the immunized and control mice. Recovery of mice that had been immunized with two i.g. doses of MVA HA-NP was seen in nasal titers (FIG. 4A). Lung virus titers were significantly lower than either naive mice or mice given MVA i.m. (FIG. 4B). MVA HA-NP i.g. immunized mice had titers that were significantly lower than MVA-HA-NP i.m. immunized mice.

TABLE 3

Splenic cytotoxic T-lymphocyte activity of mice convalescent from H1N1 infection of vaccinated i.g. with MVA HA-NP*. Data are mean % $^{51}$Cr release from H3N2-sensitized P815 cells at two different effector: target ratios.
Negative controls showed <5% lysis.

Mean % lysis of H3N2-sensitized P815 cells by mice inoculated with:

| H1N1 intranasal | | MVA HA-NP i.g. × 2 | |
|---|---|---|---|
| 30:1 | 10:1 | 30:1 | 10:1 |
| 60 | 59 | 23 | 14 |
| 59 | 57 | 21 | 17 |
| 13 | 16 | 12 | 12 |

*Spleens were obtained from BALB/c (H-2d) mice two weeks post inoculation with 108 pfu of MVA HA-NP, PR8 infection, or wild-type MVA; cultured for 7 days with H3N2-sensitized autologous splenocytes; and tested in a 6-hr 51 Cr release assay against H3N2-sensitized P815 (H-2d) cells [Bender et al., 1991; Bender et al., 1993]. Percent specific lysis was determined as [(experimental release-spontaneous release)/(total release-spontaneous release)] × 100. Spontaneous release was <10% or total.

It should be understood that the examples and embodiments described herein are for illustrative purposes only and that various modifications or changes in light thereof will be suggested to persons skilled in the art and are to be included within the spirit and purview of this application and the scope of the appended claims.

References

Andrew, M. E., B. A. H. Coupar, D. B. Boyle, G. C. Adam (1987) "The roles of influenza virus hemagglutinin and nucleoprotein in protection: analysis using vaccinia virus recombinants," Scand. J. Immunol. 25:21–28.

Arita, I. (1973) International Symposium on Smallpox Vaccine; Symposium Series in Immunobiological Standardization, Basel, Karger 19:79–87.

Bender, B. S., M. P. Johnson, C. Flexher, B. Moss, P. A. Small, Jr. (1990) "Cytotoxic T-lymphocyte activity induced by influenza vaccination in young and aged mice," In: Vaccines 90 (Brown, F., Chanock, R., Ginsberg, H. S., Lerner, R. A., eds.) Cold Spring Harbor Laboratory Press, Cold Spring Harbor, N.Y., pp. 69–73.

Bender, B. S., M. P. Johnson, P. A. Small, Jr. (1991) "Influenza in senescent mice: impaired cytotoxic T-lymphocyte activity is correlated with prolonged infection," Immunology 72:514–519.

Bender, B. S., et al. (1992) J. Exp. Med. 175:1143.

Bender, B. S., W. E. Bell, P. A. Small, Jr. (1994) J. Infect. Dis. 170:1195.

Bennink; J. R., J. W. Yewdell, G. L Smith, C. Moller, B. Moss (1984) "Recombinant vaccinia virus primes and stimulates influenza hemagglutinin-specific cytotoxic T cells," Nature 311:578–579.

Bergmann, K. C., R. H. Waldman (1988) "Stimulation of secretory antibody following oral administration of antigen," Rev. Infect. Dis. 10:939–950.

Blancou J., M. P. Kieny, R. Lathe, J. P. Lecocq, P. P. Pastoret, J. P. Soulebot, J. P. Desmettre (1986) "Oral vaccination of the fox against rabies using a live recombinant vaccinia virus," *Nature* 322:373–375.

Bloom, B. R. (1989) "Vaccines for the third world," *Nature* 342:115–120.

Brandtzeag, P. (1989) *Current Topics Microbiol. Immunol.* 146:13.

Cadoz, M., A. Strady, B. Meignier, J. Taylor, J. Tartaglia, E. Paoletti, S. Plotkin (1992) "Immunisation with canarypox virus expressing rabies glycoprotein," *The Lancet* 339:1429–1432.

Centers for Disease Control (1991) *MMWR* 40(RR-14):1–10.

Cross, R. M., C. Kaplan, D. McClean (1957) *The Lancet* 1:446.

Fenner, F., D. A. Henderson, I. Arita, Z. Jezek, I. D. Ladmyi (1988) "Smallpox and its eradication," World Health Organization, Geneva, 465.

Flexner, C., A. Hugin, B. Moss (1987) "Prevention of vaccinia virus infection in immunodeficient mice by vector-directed IL-2 expression," *Nature* 330:259–262.

Gibons, A. (1994) "Childrens' Vaccine Initiative Stumbles," *Science* 265:1376–1377.

Greer, K. E., C. N. Sheap (1974) "A family outbreak of oral accidental vaccinia," *Arch Dermatol.* 110:107–108.

Hochstein-Mintzel, V., H. C. Huber, H. Stickl (1972) "Oral and nasal immunization with poxvirus vaccinae 3rd communication: animal experiments," *Zentralb. Bacteriol.* (orig B) 156:30–96.

Kanesaki, T., B. R. Murphy, P. L. Collins, P. L Ogra (1991) "Effectiveness of enteric immunization in the development of secretory immunoglobulin A response and the outcome of infection with respiratory syncytial virus," *Journal of Virology* 65(2):657–663.

Lin, Y. L, B. A. Asknonas (1981) "Biological properties of an influenza A virus-specific killer T cell clone: inhibition of virus replication in vivo and induction of delayed-type hypersensitivity reactions," *J. Exp. Med.* 154:225–234.

Loosli, G. G., D. Hamie, B. S. Berlin (1953) "Air-borne influenza virus A infections in immunized animals," *Trans. Assoc. Am. Phys.* 66:222–230.

Mazanec, M. B., et al., (1992) *Proc. Natl. Acad. Sci USA* 89:6901.

Mazanec, M. B., C. L. Coudret, D. R. Fletcher (1995) *J. Virol.* 69:1339.

Mayr, A., V. Hochstein-Mintzel, H. Stickl (1975) *Infection* 3:6.

Mayr, A., H. Stickl, H. K. Muller, K. Danner, H. Singer (1978) *Zbl. Bakt. Hyg; I Abt. Org B.* 167:375–390.

Mayr, A., K. Danner (1979) *Berl. Munch. Tierarztl. Wochenschr* 92:251.

Meitin, C. A., B. S. Bender, P. A. Small, Jr. (1991) "Influenza immunization: intranasal live vaccinia recombinant contrasted with parenteral inactivated vaccine," *Vaccine* 9:751–756.

Meitin, C. A., P. A. Small, Jr. (1993) "Searification with a vaccinia-influenza recombinant does not stimulate IgA unless the animals auto- or cross-inoculate their nasopharynxes," *Vaccine* 11:1360–1361.

Meitin, C. A., B. S. Bender, P. A. Small, Jr. (1994) *Proc. Natl. Acad. Sci. USA* 91:11187.

Meyer, H., G. Sutter, A. Mayr (1991) *J. Gen. Virol.* 72:1031.

McGjee, J. R., J. Mestecky (1990) *Infect Dis Clinic North Am.* 4:315.

McGhee, J. R., et al. (1992) *Vaccine* 10:75.

Novak, J. D., D. B. Gowins (1984) *Learning How to Learn*, Cambridge University Press, New York.

Perkus, M. E., A. Piccini, B. R. Lipinskas, E. Paoletti (1985) "Recombinant vaccinia virus: immunization against multiple pathogens," *Science* 229:981–984.

Renegar, K. B., P. A. Small, Jr. (1991a) "Immunoglobulin A mediation of murine nasal anti-influenza virus immunity," *J. Virol.* 65:2146–2148.

Renegar, K. B., P. A. Small, Jr. (1991b) "Passive transfer of local immunity to influenza virus infection by IgA antibody," *J. Immunol.* 146:1972–1978.

Robbins, A., P. Freeman (1988) *Scientific American* 126–133.

Rota, P. A., B. K. De, M. W, Shaw, R. A Black, W. C. Gamble, A. P. Kendal (1990) "Comparison of inactivated, live and recombinant DNA vaccines against influenza virus in a mouse model," *Virus Research* 16:83–94.

Rupprecht, C. E., T. J. Wiktor, D. H. Johnston, A. M. Hamir, B. Dietzchold, W. H. Wunner, L. T. Gliekman, H. Koprowski (1986) "Oral immunization and protection of raccoons (*Procyon lotor*) with a vaccinia-rabies glycoprotein recombinant virus vaccine," *Proc. Natl. Acad. Sci. USA* 83:7947–7950.

Rupprecht, C. E., M. P. Kieny (1988) "Development of a vaccinia-rabies glycoprotein recombinant virus vaccine," In: *Rabies: Developments in Veterinary Virology* (Campbell, J. B., CharItoh, K. M., eds), Kluwer Academic Publisher, Boston, p. 335.

Rupprecht, C. E., C. A. Hardon, L. B. Cummins, H. Koprowski (1992) "Primate responses to a vaccinia-rabies glyeoprotein recombinant virus vaccine," *Vaccine* 10:368–374.

Small, P. A., Jr., G. L. Smith, B. Moss (1985) "Intranasal vaccination with recombinant vaccinia containing influenza hemagglutinin prevents both influenza viral pneumonia and nasal infection: Intradermal vaccination prevents only viral pneumonia," In: *Vaccines 85* (Lerner, R. A., Chanock, R. M., Brown, F., eds.), Cold Spring Harbor Laboratory, Cold Spring Harbor, N.Y., pp. 175–177.

Smith, G. L, B. Moss (1983) "Infectious poxvirus vectors have capacity for at least 25000 base pairs of foreign DNA," *Gene* 25:21–28.

Smith, G. L, B. R. Murphy, B. Moss (1983) "Construction and characterization of an infectious vaccinia virus recombinant that expresses the influenza hemagglutinin gene and induces resistance to influenza virus infection in hamsters," *Proc. Natl. Acad. Sci. USA* 80:7155–7159.

Stickl, A. H., British Patent No. 1-333-512, published Oct. 10, 1973.

Stickl, H., et al. (1974) *Dtsch, Med. Wochenschr.* 99:2386.

Sutter, G., and B. Moss (1992) *Proc. Natl. Acad. Sci. USA* 89:10847.

Sutter, G., L. S. Wyatt, P. L. Foley, J. R. Bennink, B. Moss (1994) "A recombinant vector derived from the host range-restricted and highly attenuated MVA strain of vaccinia virus stimulates protective immunity to influenza virus" *Vaccines* 12:1032–1040.

Wells, M. A., F. A. Ennis, P. Albrecht (1981) "Recovery from a viral respiratory infection: II Passive transfer of immune spleen cells to mice with influenza pneumonia," *J. Immunol.* 126:1042–1046.

Werner, G. T., J. Jentsch, E. Metzger, and J. Simon (1980) *J. Arch. Virol.* 64:247–256.

World Bank (1993) Investing in Health, Oxford University Press

Wu, H.-Y., M. W. Russell (1993) "Induction of mucosal immunity by intranasal application of a streptococcal surface protein antigert with the cholera toxin B subunit," *Infect. Immun.* 61:314–322.

Yap, L. L., G. L. Ada, I. F. C. McKenzie (1978) "Transfer of specific cytotoxic T lymphocytes protects mice inoculated with influenza virus," *Nature* 273:238–239.

Yetter, R. A., S. Lehrer, R. Ramphal, P. A. Small, Jr. (1980) "Outcome of influenza infection: Effect of site of initial infection and heterotypic immunity," *Infect. Immun.* 29:654–662.

We claim:

1. A method for oral or intragastric vaccine administration which comprises administering a replication deficient recombinant vaccinia or pox virus to a host under circumstances that result in delivery of said vaccine to the small intestine such that said vaccinia or pox virus is protected from exposure to stomach acid or bile, wherein said host is pre-treated, prior to said vaccine administration, such that stomach acid and bile is limited at the time that said vaccine is administered orally or intragastrically.

2. A live recombinant vaccinia pox virus or vaccinia mutant vaccine capable of expressing a heterologous polynucleotide molecule in a host, wherein said vaccine is specifically adapted to be administered to the host in a manner to induce serum IgG antibody, mucosal IgA antibody, and cell-mediated immune responses directed against said heterologous polynucleotide molecule expression product, wherein said specific adaptation comprises providing an enteric coating whereby the virus is released only when it reahces the host's small intestine, and wherein said vaccinia or poxvirus is replication deficient in mammals and wherein said heterologous polynucleotide molecule encodes an influenza virus hemagglutinin antigen, an influenza virus nucleoprotein antigen or both.

3. The vaccine, according to claim 2, wherein said recombinant vaccinia is MVA or said pox virus is canary pox virus.

4. The vaccine of claim 3, wherein said recombinant vaccinia or pox virus encodes bothe the influenza hemagglutinin and the nucleoprotein antigens.

5. A method for inducing a protective immune response in a host organism comprising immunizing a host with the vaccine according to claim 2, wherein said vaccine is enterically administered to the host.

6. A method for oral vaccine administration which comprises administering a replication deficient recombinant vaccinia or pox virus to a host under circumstances that result in delivery of said vaccine to the small intestine such that said vaccinia or pox virus is protected from exposure to stomach acid or bile, and wherein said replication deficient recombinant vaccinia or pox virus encodes an influenza virus hemagglutinim antigen, an influenza virus nucleoprotein antigen, or both.

7. The method of claim 6, wherein said recombinant vaccinia or pox virus encodes both the influenza hemagglutinin and the nucleoprotein antigens.

8. The method of claim 1 for oral vaccine administration which comprises:
   a) preparing a replication deficient recombinant vaccinia or pox virus;
   b) pre-treating a host in need of vaccination with an acid-release blocker or a cholecystokinin antagonist or both prior to orally administering said recombinant virus; and
   c) orally administering said recombinant virus.

9. The method of claim 8 wherein said virus is a recombinant MVA.

10. The method of claim 9 wherein said recombinant MVA comprises at least one influenza virus gene.

11. The method of claim 10 wherein said recombinant MVA contains an influenza virus hemagglutinin gene, an influenza virus nucleoprotein gene or both.

12. The method of claim 11 wherein said recombinant MVA is enterically coated.

* * * * *

UNITED STATES PATENT AND TRADEMARK OFFICE
CERTIFICATE OF CORRECTION

PATENT NO. : 5,676,950  Page 1 of 6
DATED : October 14, 1997
INVENTOR(S) : Parker A. Small, Bradley Stephen Bender, Catherine Ann Meitin, and Bernard Moss It is certified that error appears in the above-identified patent and that said Letters Patent is hereby corrected as shown below:

Cover page: [73] Assignee: Add --United States of America as represented by the Department of Health and Human Services, Washington, D.C.--

Cover page: References: "Intranasal Vaccination iwth" should read --Intranasal Vaccine with--

Column 1: Line 61: "Lint et at" should read --Lin et al--

Column 2: Line 54: "vaccine coffers" should read --vaccine confers--

Column 2: Line 63: "Subsequent vital" should read --subsequent viral--

Column 3: Line 8: "FIGS. 2A and 2B shows" should read --FIGS. 2A and 2B show--

Column 3: Line 19: "plotted as X $10^{-1}$ (FIG. 2)." should read --plotted as X $10^{-3}$ (FIG. 2A).--

Column 3: Line 40: " FIG. 3A and 3B shows" should read --FIG. 3A and 3B show--

UNITED STATES PATENT AND TRADEMARK OFFICE
CERTIFICATE OF CORRECTION

PATENT NO. : 5,676,950
DATED : October 14, 1997
INVENTOR(S) : Parker A. Small; Bradley Stephen Bender; Catherine Ann Meitin; Bernard Moss It is certified that error appears in the above-identified patent and that said Letters Patent is hereby corrected as shown below:

| | | |
|---|---|---|
| Column 3 | Line 63 | "FIG 4A and 4B shows" should read --FIG 4A and 4B show-- |
| Column 4 | Line 5 | "using $10^{6.5}$ ( △ ) and $10^{4.6}$ (○)" should read --using $10^{6.5}$ (▲) and $10^{4.6}$ (●)-- |
| Column 4 | Line 9 | "Day 5 pulmonary viral tiers" should read --Day 5 pulmonary 1 viral titers-- |
| Column 4 | Line 15 | "PREFERRED EMBODIMENT" should read --INVENTION-- |
| Column 5 | Line 57 | "immunized with the Vae/H1" should read --immunized with the Vac/H1-- |
| Column 6 | Line 5 | "encephalitis. Bemuse" should read --encephalitis. Because-- |
| Column 6 | Line 59 | "invention, a replication-deficient vital vector" should read --invention, a replication-deficient viral vector-- |
| Column 6 | Line 63 | "Our studies dearly demonstrate" should read --Our studies clearly demonstrate-- |
| Column 7 | Line 9 | "One i.g dose" should read --One i.m. dose-- |
| Column 7 | Line 13 | "a/L, 1991b" should read --al., 1991b-- |
| Column 7 | Line 14 | "Barber et a/l," should read --Barber et al.,-- |

UNITED STATES PATENT AND TRADEMARK OFFICE
CERTIFICATE OF CORRECTION

PATENT NO. : 5,676,950  
DATED : October 14, 1997  
INVENTOR(S) : Parker A. Small; Bradley Stephen Bender; Catherine Ann Meitin; Bernard Moss Page 3 of 6

It is certified that error appears in the above-identified patent and that said Letters Patent is hereby corrected as shown below:

| | | |
|---|---|---|
| Column 7 | Line 50 | "hours lead" should read --hours led-- |
| Column 7 | Line 66 | "a prior," should read --a priori,-- |
| Column 8 | Line 31 | "Materials and methods" should read --MATERIALS AND METHODS-- |
| Column 8 | Line 60 | "and the liters were" should read --and the titers were-- |
| Column 8 | Line 63 | "Student-Newman-Keuls post hoe test" should read --Student-Newman-Keuls post hoc test-- |
| Column 9 | Line 3 | "autologons" should read --autologous-- |
| Column 9 | Line 30 | "vaccine developed the highest liters" should read --vaccine developed the highest titers-- |
| Column 9 | Line 46 | "wash liters" should read --wash titers-- |
| Column 9 | Line 48 | "produced gut wash liters" should read --produced gut wash titers-- |
| Column 9 | Line 56 | "cant liters of" should read --cant titers of-- |
| Column 10 | Line 16 | "intragastric <0.01±0.01" should read --intragastric <0.1±0.01-- |
| Column 11 | Line 36 | "scarification, vat/H1" should read --scarification, vac/H1-- |

UNITED STATES PATENT AND TRADEMARK OFFICE
CERTIFICATE OF CORRECTION

PATENT NO. : 5,676,950
DATED : October 14, 1997
INVENTOR(S) : Parker A. Small; Bradley Stephen Bender; Catherine Ann Meitin; Bernard Moss It is certified that error appears in the above-identified patent and that said Letters Patent is hereby corrected as shown below:

| | | |
|---|---|---|
| Column 11 | Line 37 | "i.v., and vat/H1" should read -- i.v., and vac/H1-- |
| Column 11 | Line 38 | "virus tilers" should read --virus titers-- |
| Column 11 | Line 49 | "Naïve mice had high tilers" should read --Naïve mice had high titers-- |
| Column 11 | Line 58 | "antibody tiler" should read --antibody titer-- |
| Column 11 | Line 63 | "an antibody liter" should read --an antibody titer-- |
| Column 12 | Line 36 | "Female BA1b/c" should read --Female BALB/c-- |
| Column 12 | Line 50 | "(Squibb, Priceton, N.J.)" should read --(Squibb, Princeton, N.J.)-- |
| Column 12 | Line 50 | "ofPBS" should read --of PBS-- |
| Column 12 | Line 52 | "1" (2.5 era)" should read --1" (2.5cm)-- |
| Column 12 | Line 54 | "For i.m. inoculations, 100 gl" should read --For i.m. inoculations, 100 $\mu$l-- |
| Column 12 | Line 60 | "were titerd" should read --were titered-- |
| Column 13 | Line 10 | "IgA antibodies is unknown but may due" should read --IgA antibodies is unknown but may be due-- |
| Column 13 | Line 24 | "sites, a phenomenon recognized as pan" should read --sites, a phenomenon recognized as part-- |

UNITED STATES PATENT AND TRADEMARK OFFICE
CERTIFICATE OF CORRECTION

PATENT NO. : 5,676,950
DATED : October 14, 1997
INVENTOR(S) : Parker A. Small; Bradley Stephen Bender; Catherine Ann Meitin; Bernard Moss It is certified that error appears in the above-identified patent and that said Letters Patent is hereby corrected as shown below:

| | | |
|---|---|---|
| Column 13 | Line 25 | "(McGhee et al, 1990;" should read --(McGhee et al., 1990;-- |
| Column 13 | Line 34 | "virus reached a peak liter" should read --virus reached a peak titer-- |
| Column 13 | Line 63 | "were removed and cultured/n" should read --were removed and cultured in-- |
| Column 14 | Line 18 | "effector: target ratios."should read --effector:target ratios-- |
| Column 14 | Line 48 | "Bender, B.S., M.P. Johnson, C. Flexher, B." should read --Bender, B.S., M.P. Johnson, C. Flexner, B.-- |
| Column 15 | Line 56 | "Searification with a" should read --Scarification with a-- |
| Column 16 | Line 17 | "D. Dietzchold, W. H. Wunner, L. T. Gliekman, H." should Read --D. Dietzhold, W. H. Wunner, L. T. Glickman, H.-- |
| Column 16 | Line 25 | "(Campbell, J. B., Charltoh" should read --(Campbell, J. B., Charlton-- |
| Column 16 | Line 29 | "rabies glyeoprotein" should read --rabies glycoprotein-- |
| Column 17 | Line 18 | "A live recombinant vaccinia pox virus or vaccinia" should read --A live recombinant vaccinia or pox virus-- |
| Column 17 | Line 19 | "mutant vaccine capable" should read --vaccine capable-- |
| Column 17 | Line 27 | "only when it reahces" should read --only when it reaches-- |

UNITED STATES PATENT AND TRADEMARK OFFICE
CERTIFICATE OF CORRECTION

PATENT NO. : 5,676,950

DATED : October 14, 1997

INVENTOR(S) : Parker a. Small, Bradley Stephen Bender, Catherine Ann Meitin, and Bernard Moss It is certified that error appears in the above-identified patent and that said Letters Patent is hereby corrected as shown below:

Column 17  Line 35  "encodes bothe the" should read --encodes both the--

Column 18  Line 12  "virus hemagglutinim antigen," should read --virus hemagglutinin antigen,--

Signed and Sealed this

Twenty-second Day of June, 1999

Attest:

Q. TODD DICKINSON

*Attesting Officer*  *Acting Commissioner of Patents and Trademarks*